(12) United States Patent
Murakami

(10) Patent No.: US 10,876,918 B2
(45) Date of Patent: Dec. 29, 2020

(54) WATER LEAKAGE DETECTOR

(71) Applicant: DENSO WAVE INCORPORATED, Aichi-pref. (JP)

(72) Inventor: Yotaro Murakami, Chita-gun (JP)

(73) Assignee: DENSO WAVE INCORPORATED, Aichi-pref. (JP)

( * ) Notice: Subject to any disclaimer, the term of this patent is extended or adjusted under 35 U.S.C. 154(b) by 320 days.

(21) Appl. No.: 15/907,950

(22) Filed: Feb. 28, 2018

(65) Prior Publication Data

US 2018/0275009 A1  Sep. 27, 2018

(30) Foreign Application Priority Data

Mar. 23, 2017  (JP) ................. 2017-057396

(51) Int. Cl.
| | | |
|---|---|---|
| *G01R 27/26* | (2006.01) | |
| *G01M 3/16* | (2006.01) | |
| *G01M 3/40* | (2006.01) | |
| *G01N 27/22* | (2006.01) | |
| *G01N 33/24* | (2006.01) | |
| *G01N 27/04* | (2006.01) | |
| *G01R 27/02* | (2006.01) | |
| *G01R 15/18* | (2006.01) | |
| *G01R 19/00* | (2006.01) | |

(52) U.S. Cl.
CPC ................ *G01M 3/16* (2013.01); *G01M 3/40* (2013.01); *G01N 27/048* (2013.01); *G01N 27/223* (2013.01); *G01N 27/225* (2013.01); *G01N 33/246* (2013.01); *G01R 15/186* (2013.01); *G01R 19/0084* (2013.01); *G01R 27/02* (2013.01); *G01R 27/2605* (2013.01)

(58) Field of Classification Search
CPC .. G01N 27/223; G01N 33/246; G01N 27/225; G01N 27/048; G01R 27/2605; G01R 27/02; G01R 15/186; G01R 19/0084
USPC .......... 324/76.11–76.83, 600, 634, 640, 643, 324/649, 658, 663, 664, 689, 694
See application file for complete search history.

(56) References Cited

U.S. PATENT DOCUMENTS

| | | | | |
|---|---|---|---|---|
| 2004/0199131 A1* | 10/2004 | Kitamura | ................ | A61F 5/451 604/318 |
| 2005/0285608 A1* | 12/2005 | Sato | .................... | G01N 27/226 324/663 |
| 2009/0244833 A1* | 10/2009 | Imamura | ............... | G06F 1/1616 361/679.55 |

(Continued)

FOREIGN PATENT DOCUMENTS

| | | |
|---|---|---|
| JP | 4081954 B2 | 4/2008 |
| JP | 4999493 B2 | 8/2012 |

OTHER PUBLICATIONS

KR 2005-0053320 Machine Translation Dec. 2, 2003. (Year: 2003).*

*Primary Examiner* — Raul J Rios Russo
(74) *Attorney, Agent, or Firm* — Oliff PLC

(57) ABSTRACT

A water leakage detector includes: an electrostatic capacity sensor that is arranged at a bottom portion of a housing; and a leg portion that provides a space between the bottom portion and a floor of the housing including the electrostatic capacity sensor. With this configuration, it may be possible to detect quickly in an earlier stage of water leakage and achieve resistance to deterioration caused by an environment.

14 Claims, 12 Drawing Sheets

(56) References Cited

U.S. PATENT DOCUMENTS

2009/0323262 A1* 12/2009 Arita .................. H04M 1/23
361/679.01

* cited by examiner

TO CONTROL BOARD

TO CONTROL BOARD

FIG. 13
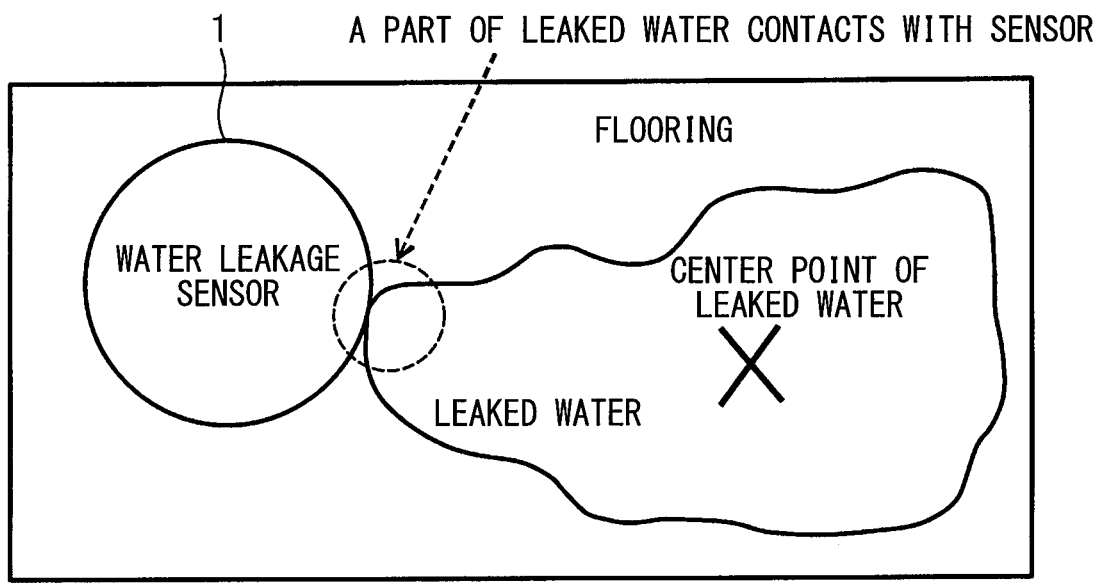
FIG. 14A
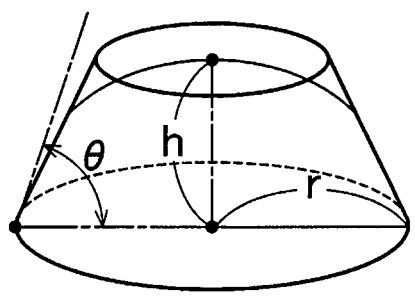
FIG. 14B
$$V = \frac{1}{3}\pi \left\{ r^3 \tan\theta - h\left(r - \frac{h}{\tan\theta}\right)^2 \right\}$$

| FLOOR MATERIAL | STEEL PLATE | TILE | FLOORING | CARPET |
|---|---|---|---|---|
| CONTACT ANGLE (MEASURED VALUE) | 10° | 20° | 45° | 80° |
| HEIGHT OF WATER DROPLET (MEASURED VALUE) | 1mm | 1.4mm | 1.5mm | 4mm |
| RADIUS r (MEASURED VALUE) | 6mm | 5mm | 4mm | 3mm |
| RADIUS r (CALCULATED VALUE) | 6.5mm | 5.6mm | 4.5mm | 3.1mm |
| ERROR | 8.3% | 12.0% | 12.5% | 3.3% |

GROOVE WIDTH $x = 2 \times (r - h/\tan\theta)$

WATER LEAKAGE DETECTOR

CROSS REFERENCE TO RELATED APPLICATIONS

This application is based on Japanese Patent Application No. 2017-057396 filed on Mar. 23, 2017, the disclosure of which is incorporated herein by reference.

TECHNICAL FIELD

The present disclosure relates to a detector that detects water leakage mainly on a floor of a house or the like.

BACKGROUND

Patent Literature 1: JP 4081954 B
Patent Literature 2: JP 4999493 B

Various techniques for detecting water leakage of a water pipe have been proposed. In recent years, a water supply facility as an infrastructure may become deteriorated nationwide. Accordingly, the inventor of the present application has found that it may be desirable that the water leakage is detected when slight water leakage occurs and measures are taken in an earlier stage from a viewpoint of preventing waste of water or damage of the house. As conventional water leakage detectors, a resistance type detector (Patent Literature 1) and an optical type detector (Patent Literature 2) are known, and such detectors detect the water leakage when water is contacted with a detection portion directly.

SUMMARY

The detectors disclosed in Patent Literatures 1 and 2 cannot detect the water leakage during a period when water is not contacted with the detection portion. In general, in an initial stage of the water leakage, a small amount of water leaked from the water pipe is transferred gradually to spread on a wall surface, a floor, or the like of the house. Thus, for example in a case where a mat such as a carpet is arranged on the floor and the water leakage detector is arranged on the mat, the water is absorbed by the carpet. Consequently, the water leakage may not be detected until the damage is spread to some extend because the water leakage detector cannot detect the water leakage until a leaked water amount becomes large enough to be oozed from the carpet. Further, in the configurations disclosed in Patent Literature 1 and 2, since the detection portion is exposed, the detection performance may be deteriorated due to oxidation or adhesion of foreign objects.

It is an object of the present disclosure to provide a water leakage detector being capable of detecting quickly in an earlier stage of water leakage and having resistance to deterioration caused by an environment.

According to one aspect of the present disclosure, a water leakage detector includes: an electrostatic capacity sensor that is arranged at a bottom portion of a housing; and a leg portion that provides a space between the bottom portion and a floor of the housing including the electrostatic capacity sensor.

According to this configuration, when the water leakage detector is arranged on the floor such as flooring and a carpet, an air layer is formed between the bottom portion of the housing and the floor. Thus, the electrostatic capacity sensor acquires an electrostatic capacity value based on a dielectric constant of air in a state where the water leakage does not occur. In a case where the floor is formed of the flooring, when water is entered into the space below the bottom portion of the housing of the water leakage detector, it may be possible to detect the water leakage by using the electrostatic capacity value changed based on a dielectric constant of the water. In a case where the floor is formed of the carpet, when the water is oozed from the carpet below the bottom portion of the housing, it may be possible to detect the water leakage similarly by using the electrostatic capacity value changed based on the dielectric constant of the water. That is, it may be possible to detect the water leakage quickly on both of the flooring and the carpet.

According to another aspect of the present disclosure, a water leakage detector includes: an electrostatic capacity sensor that is arranged at an inner bottom of a housing; an electronic component that performs communication or input processing of the electrostatic capacity sensor, the electronic component being arranged in the housing; and multiple leg portions that are arranged at an outer bottom surface of the housing.

According to this configuration, when the water is located at the bottom portion of the housing separated from the mount surface of the water leakage detector by a length of the leg portion, the dielectric constant between the bottom portion of the housing and the mount surface is changed from the value of air to the value of water, and therefore the electrostatic capacity is changed. The electrostatic capacity sensor detects the change of the electrostatic capacity, and thereby the water leakage can be detected in a case where the water is not contacted with the sensor directly. Accordingly, it may be possible to detect the water leakage quickly, and to restrict the spread of the damage at minimum.

According to this configuration, in the water leakage detector, since the electrostatic capacity sensor and the electronic component are arranged in the housing, it may be possible to completely separate those components from water. When the water leakage is detected, the water does not adhere to the sensor and therefore the sensor is not deteriorated due to a foreign object in the water. Since the water does not adhere to the electronic component, the circuit is not short-circuited. Accordingly, it may be possible to use the water leakage detector repeatedly for several times for a long period of time.

Therefore, it may be possible to detect quickly in an earlier stage of water leakage and achieve resistance to deterioration caused by an environment.

BRIEF DESCRIPTION OF DRAWINGS

The above and other objects, features and advantages of the present disclosure will become more apparent from the following detailed description made with reference to the accompanying drawings. In the drawings:

FIG. 13 is a view illustrating a state in which leaked water spread on a floor is contacted with a side surface of the water leakage detector;

FIG. 14A is a view illustrating a water droplet modeled into a truncated cone;

FIG. 14B is a view illustrating a water droplet modeled into a truncated cone;

DETAILED DESCRIPTION

First Embodiment

Figure 1:
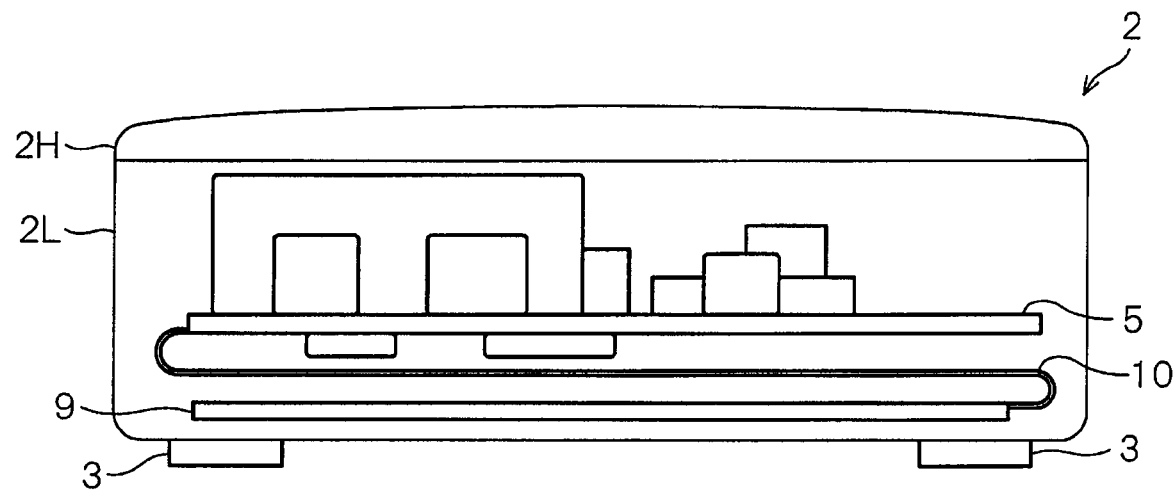
FIG. 1 is a transparent side view of a water leakage detector according to at least one of embodiments.
Figure 2:
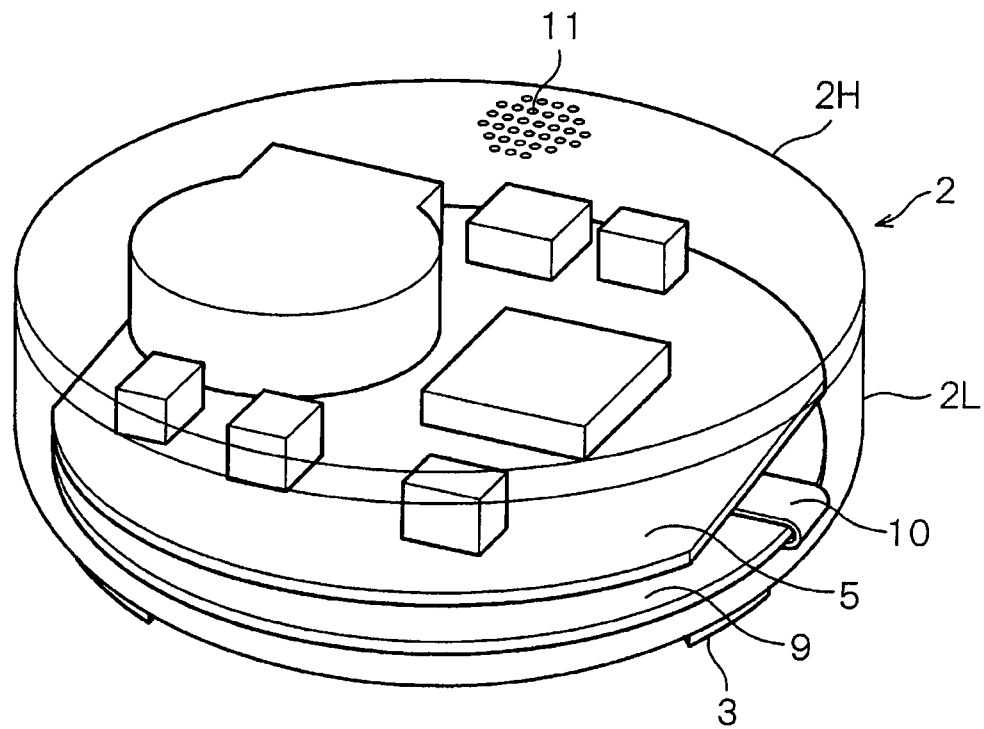
FIG. 2 is a transparent perspective view of the water leakage detector.
Figure 3:
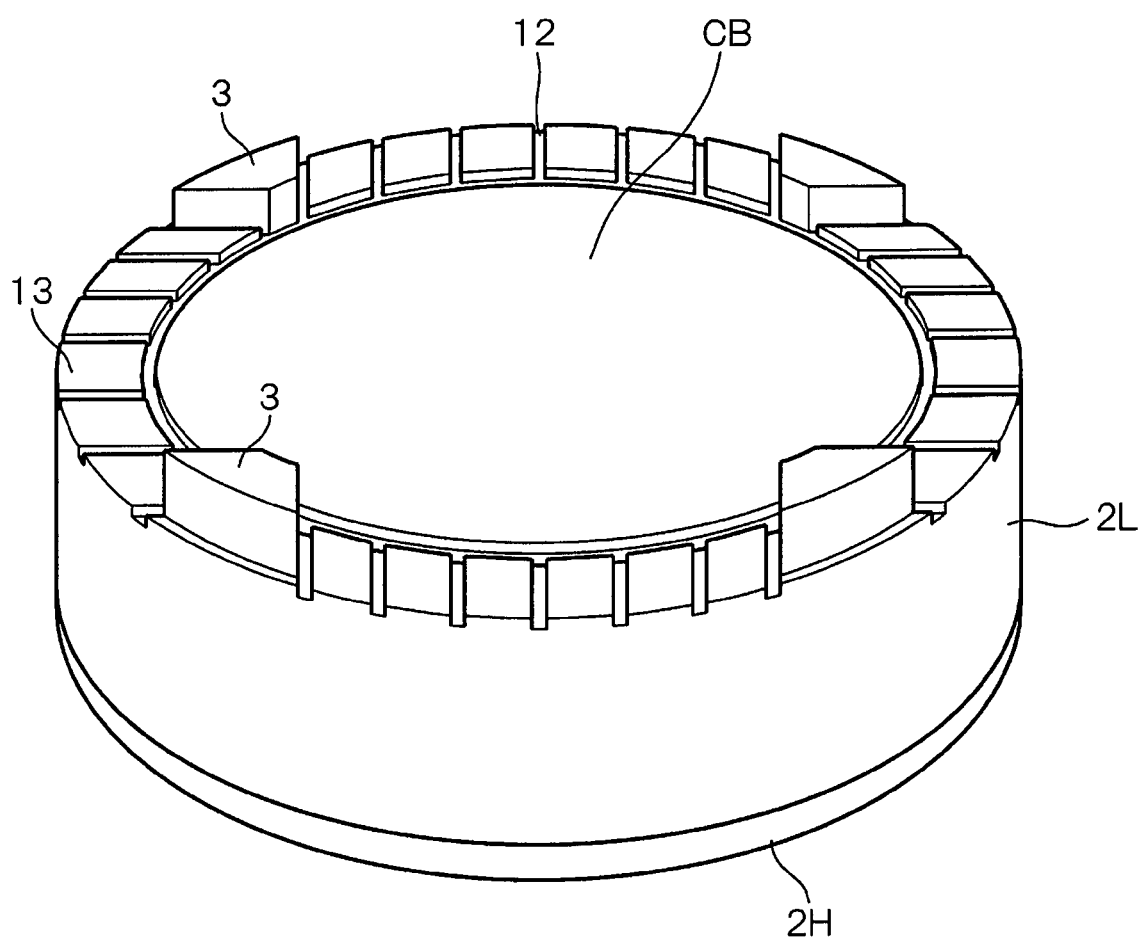
FIG. 3 is a perspective view of an outer bottom surface of the water leakage detector.

Hereinafter, a first embodiment will be described with reference to FIG. 1 to FIG. 16B. FIG. 1 is a transparent side view of the inside of a water leakage detector. FIG. 2 is a transparent perspective view of the inside of the water leakage detector. FIG. 3 is a perspective view of an outer bottom surface of the water leakage detector. A water leakage detector 1 includes a case 2 formed as a cylindrical housing. Four studs 3 corresponding to leg portions are arranged at parts of a bottom portion of the case 2. The case 2 includes a lower case 2L opened at an upper surface thereof and an upper case 2H that is in a lid shape and covers the opening of the lower case 2L. The lower case 2L houses therein a component configuring a sensor or the like, and a control board 5.

Figure 10:
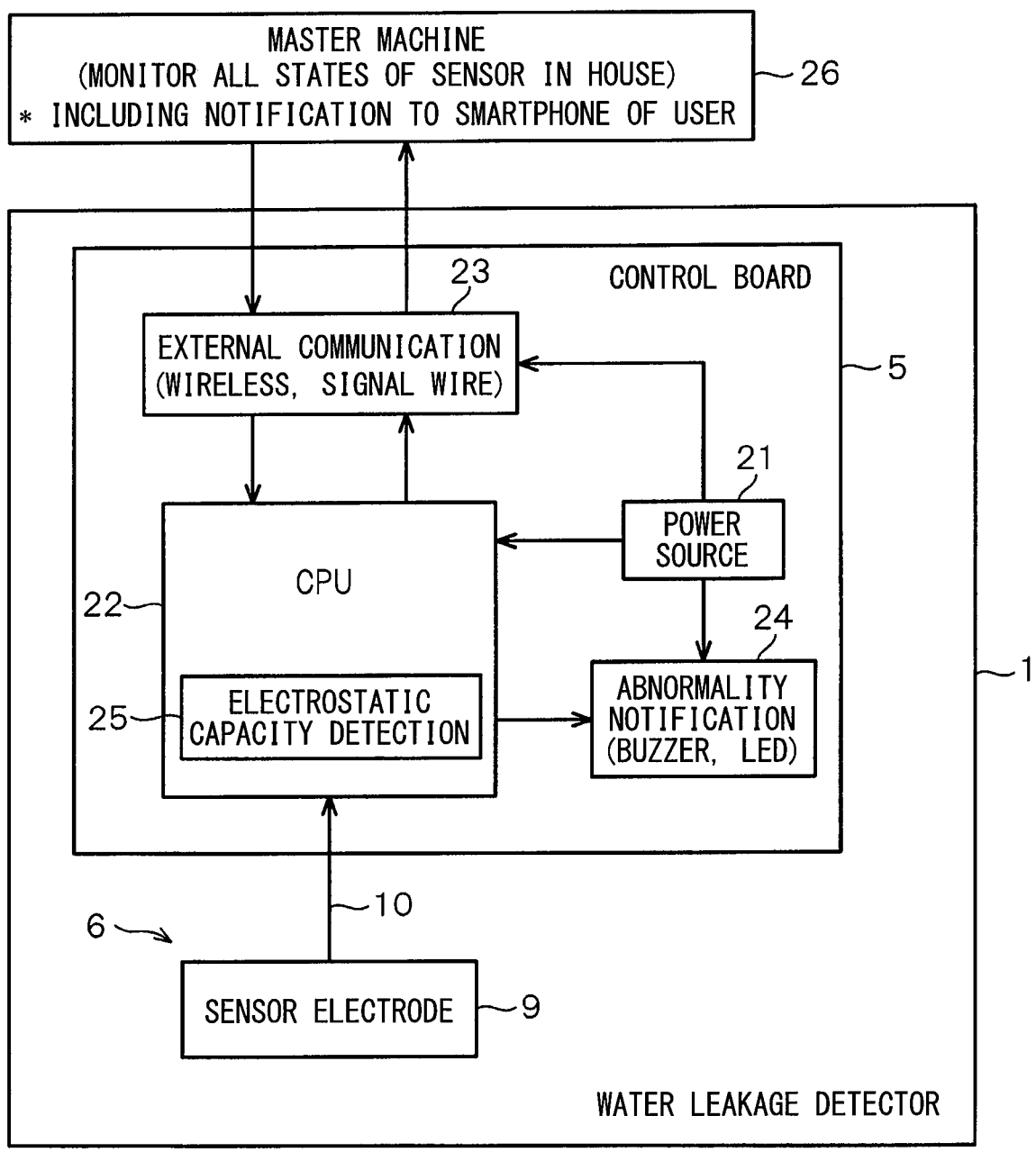
FIG. 10 is a block diagram illustrating an electrical configuration of the water leakage detector.

The water leakage detector 1 includes an electrostatic capacity sensor 6 shown in FIG. 10 that detects water leakage in a noncontact manner in a state where the water leakage detector 1 is arranged on a floor or the like. The electrostatic capacity sensor 6 includes detection electrodes 7 (also referred to as detection electrodes 7a to 7d) and a ground electrode 8 shown in FIG. 7, FIG. 8, or the like. These electrodes are called a sensor electrode portion 9. The sensor electrode portion 9 is arranged on an inner bottom surface of the lower case 2L and electrically connected to the control board 5 arranged above the sensor electrode portion 9 via an FPC (flexible printed circuit) cable 10. The upper case 2H has multiple through holes 11 emitting, to an outside, sound of a buzzer driven or light of an LED turned on when the water leakage is detected. The electrostatic capacity sensor may be referred to as an electrostatic capacity type sensor.

Here, an arrangement configuration of the FPC cable 10 is not limited to the case shown in drawings. Further, the sensor electrode portion 9 may be formed by, for example, insert molding of printing an electrode pattern directly in the inside of the lower case 2L.

Figure 4:
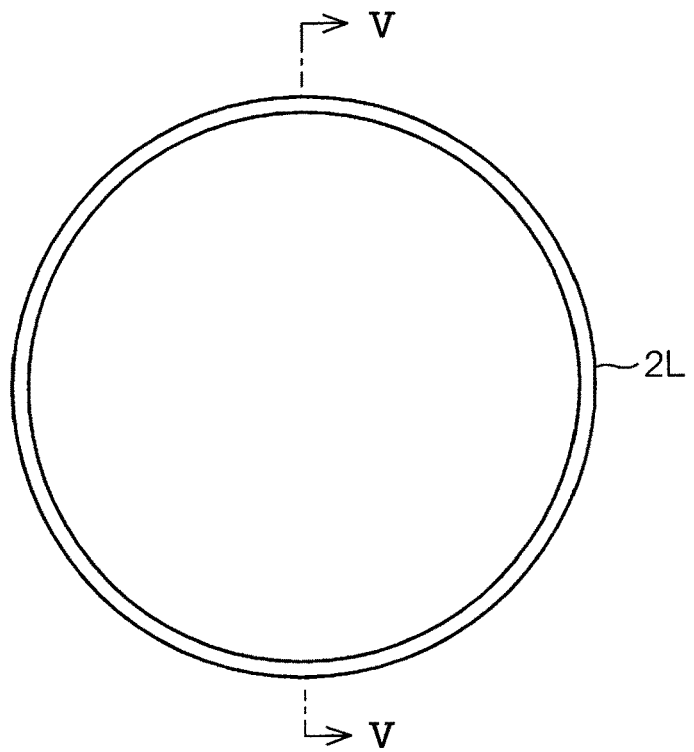
FIG. 4 is a plan view of a lower case.
Figure 5:
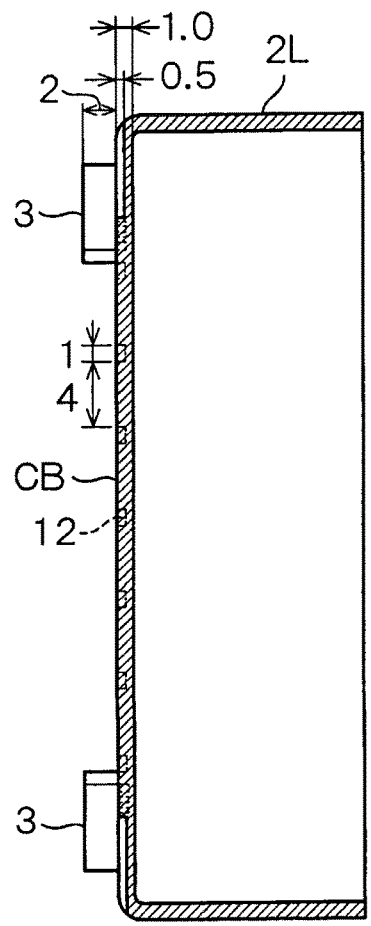
FIG. 5 is a vertical cross-sectional side view of the lower case.

FIG. 4 is a plan view of the lower case 2L, and FIG. 5 is a vertical cross-sectional side view of the lower case 2L. As shown in FIG. 3, FIG. 5, or the like, multiple water introducing grooves 12 are arranged in parallel with each other at intervals on an outer peripheral portion of an outer bottom surface CB of the lower case 2L. The water introducing grooves 12 are formed in four directions between the four studs 3 respectively. Further, a water preventing groove 13 having a circular shape is formed to communicate end portions of an inner peripheral side of the water introducing grooves 12. As one example shown in FIG. 5, a height of each stud 3 is 2 mm, a width of each groove 12 is 1 mm, and the interval between the water introducing grooves 12 is 4 mm. Further, a thickness of a bottom of the lower case 2L is 1 mm, and a depth of the groove 12 is 0.5 mm.

Next, the reason for setting the size in such a way will be described with reference to FIG. 13 to FIG. 16B. Surface tension applied to water works as resistance when a surface area of the water is changed. That is, force of a certain level or more is necessary to change the surface area of the water. In a case of water leakage of a small amount, force which pushes the water from the side surface of the water leakage detector toward the outer bottom surface is small. Accordingly, for example as shown in FIG. 13, when the leaked water reaches the side surface after approaching from a side surface direction of the sensor and the detector, and the space toward the outer bottom surface into which the water enters is small against the surface area of the water entered from the side surface, the water is retained on the side surface due to the surface tension, and thereby the water does not enter the outer bottom surface. Thus, in order to solve this situation described above, the outer bottom surface of the water leakage detector 1 is formed such that a change of the surface area of water becomes small.

As shown in FIG. 14A and FIG. 14B, it is assumed that a shape of the water droplet having a volume V when the water is contacted with a solid surface and dropped can be approximated by a truncated cone of a radius r and a height h. At this time, an angle between the solid surface and the water droplet is defined as a contact angle θ. The contact angle θ is determined based on a floor material. The above parameters are represented by using a relational equation below.

$$V = \pi/3 \{ r^3 \tan\theta - h(r - h/\tan\theta)^2 \} \tag{1}$$

Here, the height h of the water droplet is maximum when the contact angle θ=180°, namely when the shape of the water droplet is a sphere. As the volume V=0.083 mL of the water droplet is defined based on the experimental value, the height h of the water droplet from the solid surface is 5.4 mm at maximum. Accordingly, in order to contact the water with the outer bottom surface CB of the water leakage detector 1 regardless of the floor material, it is necessary to set the height of the surface CB with which the water is contacted is set to 5.4 mm or less.

Figures 15, 16A, 16B:
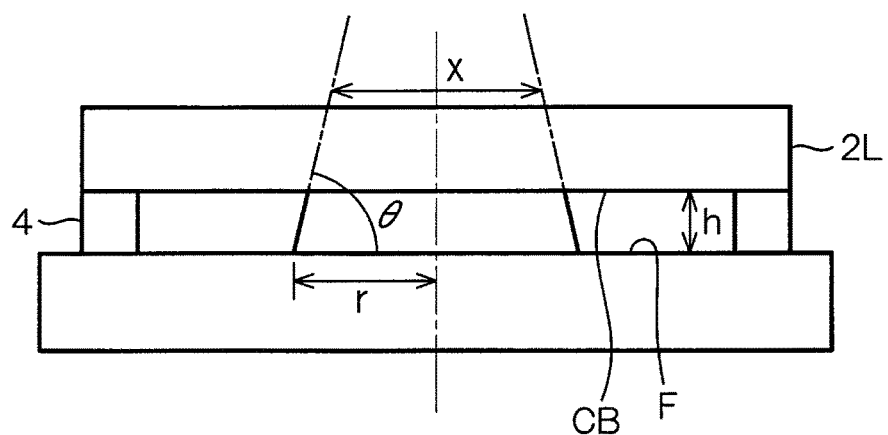
FIG. 15 is a diagram illustrating theoretical values and measured values of a contact angle θ, a height h, and a radius r in a case where a water droplet having the same volume is contacted with several floor materials.
FIG. 16A is a view illustrating a calculation formula of a groove width x.
FIG. 16B is a view illustrating a calculation formula of a groove width x.

FIG. 15 illustrates theoretical values and measured values of the contact angle θ, the height h, and the radius r in a case where the water droplet having the volume V=0.083 mL is contacted with several floor materials. Examples of the solid having a small contact angle θ in a living environment include glass and a steel plate which have a contact angle θ of approximately 10°, and have a height h equal to approximately 1 mm. That is, by setting the height h of the sensor to be less than 1 mm, the surface area of the water is inevitably changed, and therefore it is considered that the water easily enter by setting the height of the sensor to be h≥1 mm. Thus, it is concluded that the height of the outer bottom surface of the water leakage detector 1 into which the water can enter easily is in a range between 1 mm and 5.4 mm. However, it is unlikely that the water leakage detector is arranged on a super water repellent material having the contact angle θ of more than 90° in an actual usage, and therefore it is considered that the actual upper limit of the height is approximately 4 mm.

On the other hand, in a case where the height of the outer bottom surface is lower, a change of the electrostatic capacity when the water is entered becomes larger. A volume ratio of the water against volume of the air layer becomes larger. Thus, the change of the surface area of the water is set to be small by forming a groove on the outer bottom surface CB in order to make the water enter easily even in a case where the height of the outer bottom surface CB is set to be further lower, for example 1.0 mm to 2.0 mm.

That is, the groove having a width suitable for the entering water is formed on the outer bottom surface CB, and thereby the water is apt to enter the outer bottom surface CB. A configuration in which the state of the water droplet is kept as much as possible and the water spread on the floor is absorbed by the outer bottom surface CB is adopted by forming the groove having the width same as the width of the water droplet which is the most stable in energy with the surface area being minimum. Since the water droplet is stable in energy, the water droplet is apt to be retained in the groove once the water droplet enters the groove. When considered by using the model shown in FIG. 16A, as a groove width is defined as x, it is represented as $$x=2\times(r-h/\tan\theta) \qquad (2)$$

Further, as the height h from a floor surface F, which is a mount surface, to the outer bottom surface CB is set to 2.0 mm against the carpet having a material of the contact angle θ=80°, the groove width x is calculated as 4.0 mm from the formula (2). The groove width x may be adopted as the width of the groove itself or the interval between the grooves.

Figure 6:
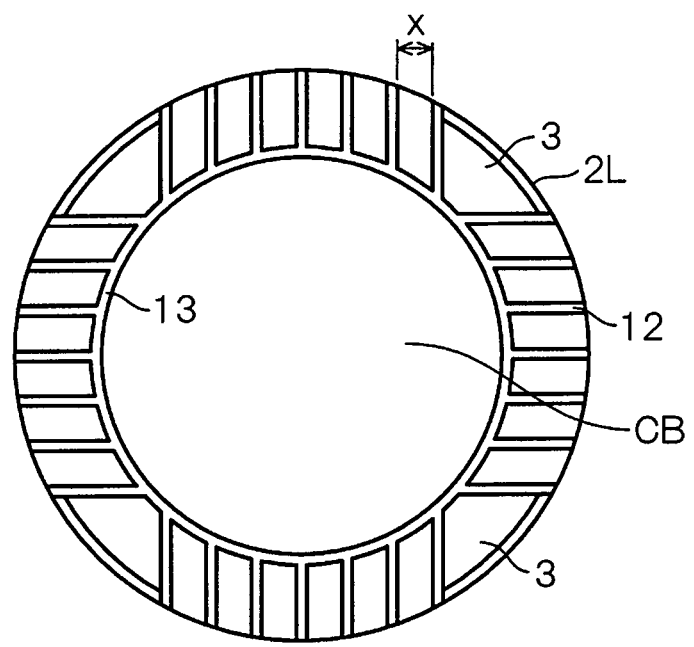
FIG. 6 is a bottom view of the lower case.
Figure 7:
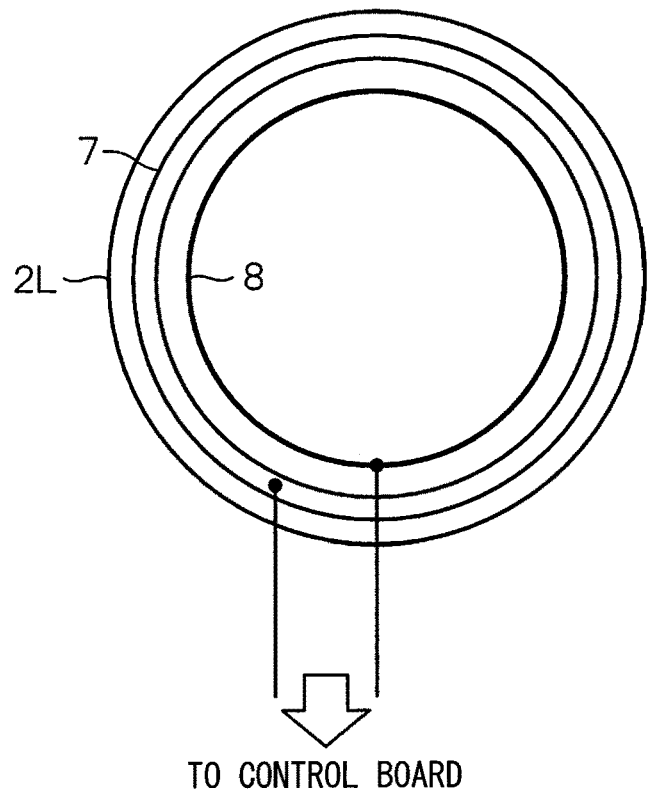
FIG. 7 is a diagram illustrating an example of a formation pattern of a detection electrode and a ground electrode.

Based on the studies described above, in the present embodiment, as shown in FIG. 3, FIG. 5, and FIG. 6, the water introducing grooves 12 are formed at intervals of 4.0 mm in four directions between the studs 3 having a height of 2.0 mm at the outer peripheral portion of the outer bottom surface CB. With this, the water that has entered the outer bottom surface CB keeps a shape of the water droplet at a position between the two grooves 12.

Next, a configuration of the sensor electrode portion 9 configuring the electrostatic capacity sensor 6 will be described. As described above, the sensor electrode portion 9 is formed by the detection electrode 7 and the ground electrode 8, and as an example shown in FIG. 7, it may be considered to arrange the detection electrode 7 and the ground electrode 8 in a doughnut shape at the outer peripheral portion. The change amount of the electrostatic capacity of the detection electrode 7 becomes larger as the electrode area of the detection electrode 7 becomes smaller, and therefore the detection sensitivity of the water leakage is improved. On the other hand, the detection electrode 7 is apt to receive the influence of noise as the electrode area of the detection electrode 7 becomes smaller.

Figure 8:
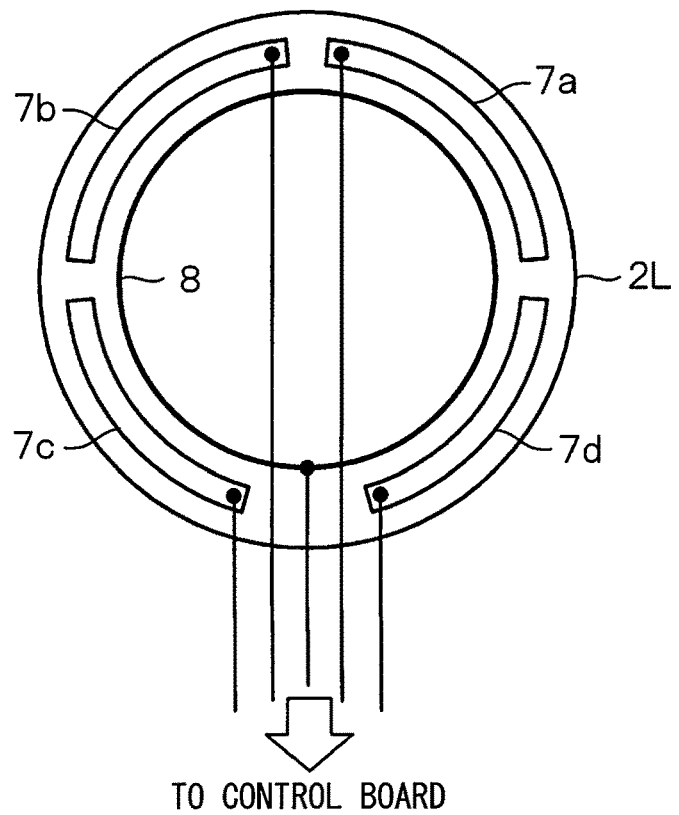
FIG. 8 is a view illustrating another example of a formation pattern of the detection electrode and the ground electrode.

Thus, in the present embodiment, as shown in FIG. 8, the detection electrode 7 is formed in a pizza shape divided into four parts, and four electrodes 7a, 7b, 7c, and 7d each having an arc shape are arranged on an inner bottom portion of the lower case 2L. Further, by dividing the detection electrode 7 in such a way, it may be possible to determine in which direction the water leakage is detected against an arrangement state of the water leakage detector 1.

Figure 9:
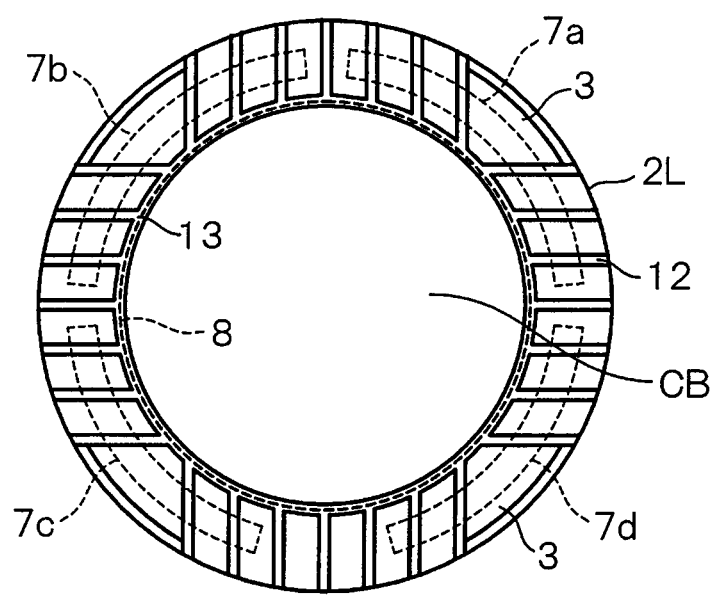
FIG. 9 is a view illustrating a formation pattern of the electrodes shown in FIG. 8 overlapped by a groove shown in FIG. 6.

FIG. 9 illustrates the detection electrodes 7a to 7d and the ground electrode 8, which are arranged in the inner bottom side of the lower case 2L, overlapped with FIG. 6. The water introducing grooves 12 are formed at positions corresponding to the detection electrodes 7a to 7d, and the water preventing groove 13 is formed at a position corresponding to the ground electrode 8. In this way, by forming the grooves 12 and 13 at the positions corresponding to the electrodes 7 and 8, the water can be retained between the detection electrode 7 and the ground electrode 8, and therefore it may be possible to enhance the detection sensitivity of the water leakage.

FIG. 10 is a block diagram illustrating an electrical configuration of the water leakage detector 1. A power source 21, a CPU 22, an external communication portion 23, an abnormality notification portion 24, and the like are installed on the control board 5. The power source 21 is formed as, for example, a button battery to supply direct current to each part. The sensor electrode portion 9 is connected to an input terminal of the CPU 22 via the FPC cable 10. The CPU 22 includes an electrostatic capacity detection portion 25 formed by hardware and software. The sensor electrode portion 9 and the electrostatic capacity detection portion 25 are components of the electrostatic capacity sensor 6. The electrostatic capacity detection portion 25 may not be necessarily formed as a function of the CPU 22, and the electrostatic capacity detection portion 25 may be formed by hardware at an outside of the CPU 22.

The external communication portion 23 allows the CPU 22 to perform the communication with a master machine 26 by wireless or wire. The CPU 22 transmits information such as occurrence of the water leakage detection, an ID of the water leakage detector 1, and a voltage level of the power source 21, to the master machine 26 via the external communication portion 23. The master machine 26 includes, for example, a monitoring panel installed in a house, a smartphone carried by a user, or the like, and the master machine 26 monitors the water leakage detector 1 based on the received information. Further, in case of the smartphone, a specific application program suitable to the present embodiment should be downloaded in advance.

The abnormality notification portion 24 is, for example, the buzzer or the LED described above. When the CPU 22 detects the water leakage, the CPU 22 activates the abnormality notification portion 24 to inform the water leakage to a user by sounding the buzzer or turning on the LED.

Figure 11:
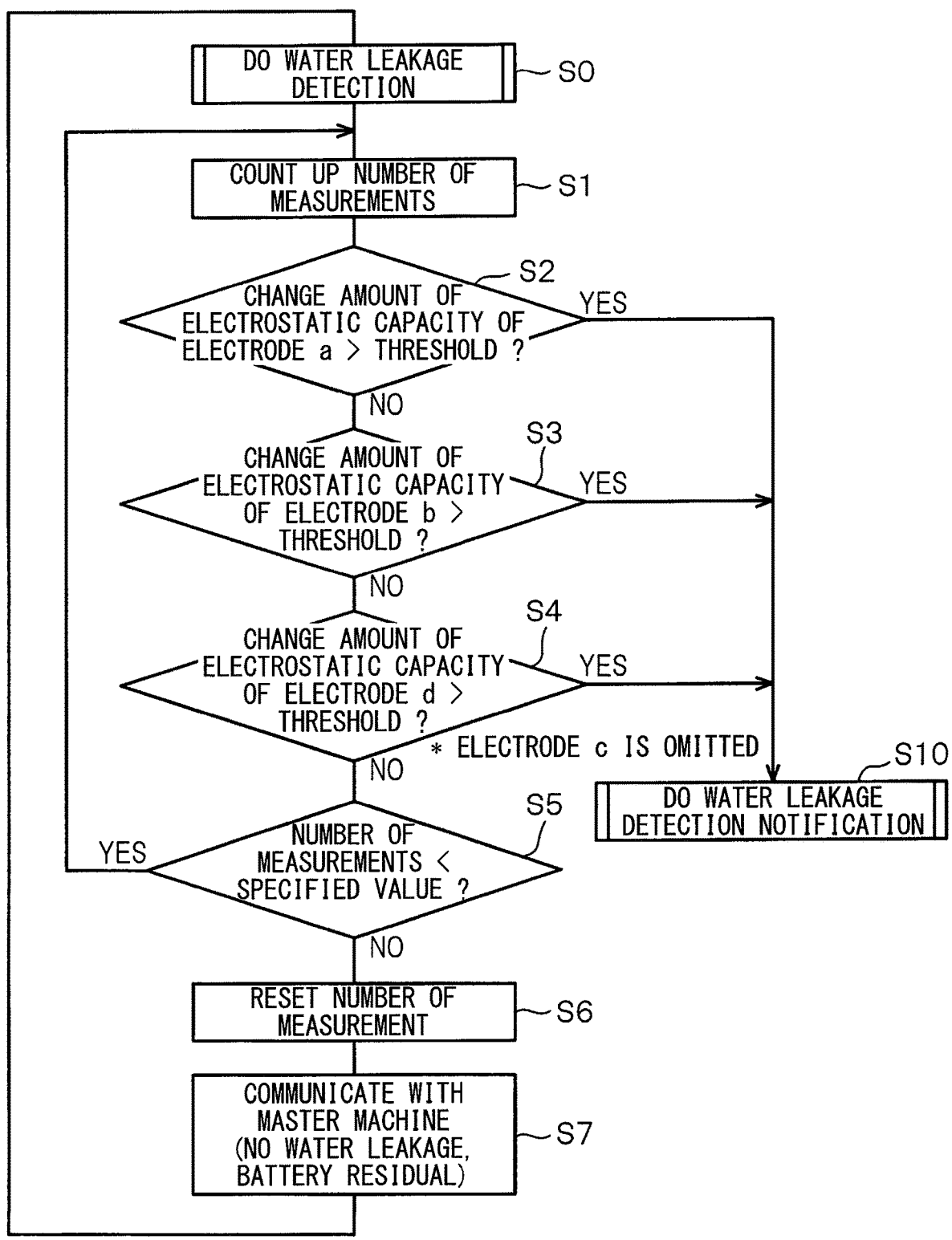
FIG. 11 is a flowchart illustrating water leakage detection processing.
Figure 12:
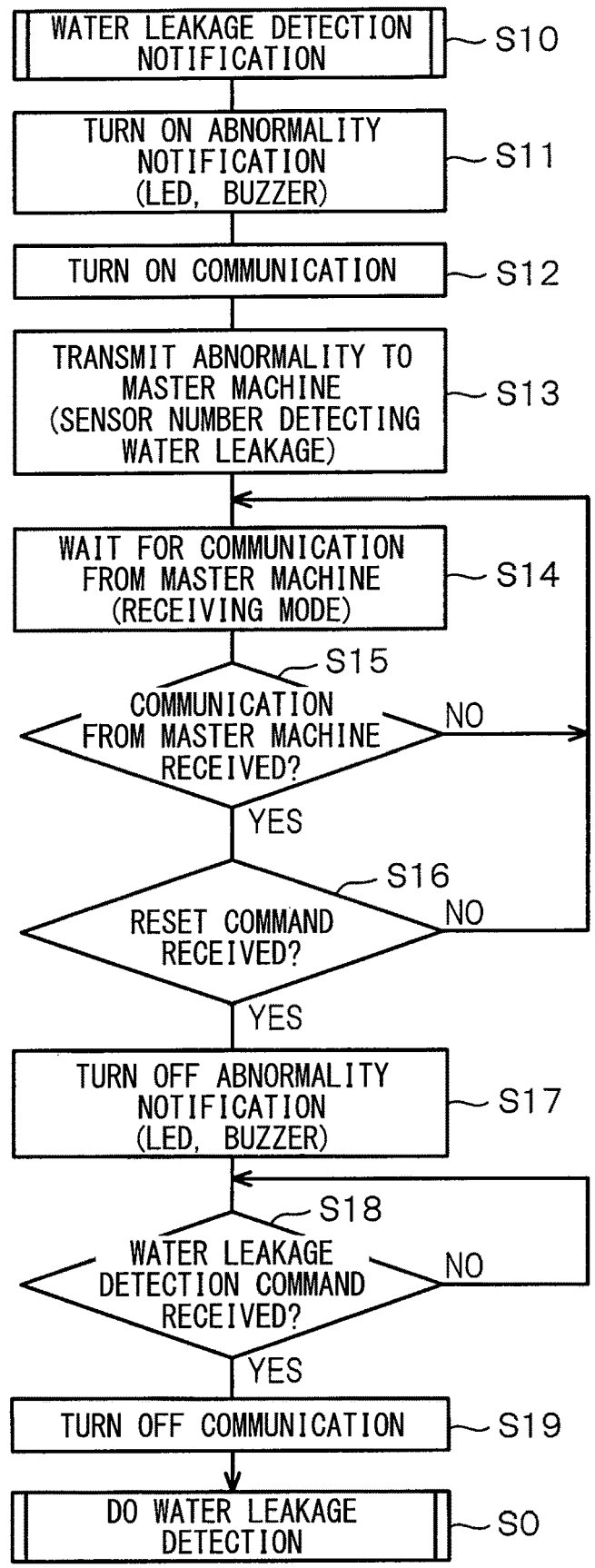
FIG. 12 is a flowchart illustrating water leakage detection notification processing.

Next, operation of the present embodiment will be described with reference to FIG. 11 and FIG. 12. FIG. 11 is a flowchart illustrating water leakage detection processing executed by the CPU 22. At first, the number of measurements is counted up (S1), and it is determined whether the change amount of the electrostatic capacity exceeds a threshold in each of the detection electrodes 7a to 7d (S2 to S4). In a case where each of the change amount does not exceed the threshold (S4; NO), it is determined whether the number of the measurements at that time is less than a predetermined specified value (S5). In a case where the number of the measurements does not reach the specified value (YES), the procedure returns to S1. On the other hand, in a case where the number of the measurements reaches the specified value (NO), the number of the measurements is reset (S6), and the communication with the master machine 26 is performed (S7). The information transmitted at this time is "no water leakage", and a battery residual and the voltage level of the power source 21.

In a case where the change amount of the electrostatic capacity of either of the detection electrodes 7a to 7d exceeds the threshold during the procedure described above (S2 to S4; YES), the procedure proceeds to the water leakage detection notification processing (S10). FIG. 12 is a flowchart illustrating the water leakage detection notification processing. At first, the abnormality notification portion 24 is driven and turned on to sound the buzzer or to turn on the LED (S11). Next, abnormality transmission is performed (S12 and S13). In the abnormality transmission, detection of the water leakage is informed to the master machine 26 via the external communication portion 23. At this time, a sensor number as the ID of the water leakage detector 1 is also transmitted. Then, in a receiving mode (S14), it is waited for the transmission from the master machine 26 (S15).

When the transmission is received from the master machine 26 (S15; YES), it is determined whether a reset command is included in the communication contents (S16). In a case where the reset command is not included (NO), the procedure returns to S14, and in a case where the reset command is included (YES), the driving of the abnormality notification portion 24 is stopped, and sounding of the buzzer is stopped and the LED is turned off (S17). Further, in a case where a water leakage detection command is included in the communication contents (518; YES), the external communication portion 23 is turned OFF (S19), and the procedure proceeds to the water leakage detection processing (S0).

Further, the procedure described above may be modified as below. Instead of proceeding to S10 immediately after it is determined as "YES" in any of S2 to S4, the procedure proceeds to S10 after all determinations of S2 to S4 are executed and it is determined as "YES" in one or more of S2 to S4. In the water leakage detection notification processing, the information relating to all steps determined as "YES" among S2 to S4 is informed, and the master machine 26 determines a direction in which the water leakage is detected. Alternatively, the direction may be determined by the CPU 22 and then the determined direction may be informed to the master machine 26.

According to the present embodiment described above, the water leakage detector 1 includes the electrostatic capacity sensor 6 arranged at the inner bottom portion of the case 2, an electronic component for performing communication processing or input processing of the sensor, the electronic component being arranged in the case 2, and the multiple studs 3 arranged on the outer bottom surface CB of the case 2. That is, the water leakage detector 1 includes the electrostatic capacity sensor 6 arranged at the bottom portion of the case 2, and the studs 3 that form a space between the bottom portion of the case 2 including the electrostatic capacity sensor 6 and a floor. With such a configuration, when the water leakage detector 1 is arranged on the floor such as flooring and a carpet, an air layer is formed between the bottom portion of the case 2 and the floor. Thus, the electrostatic capacity sensor 6 acquires an electrostatic capacity value based on a dielectric constant of air in a state where the water leakage does not occur. In a case where the floor is formed of the flooring, when water enters the space below the bottom portion of the housing of the water leakage detector 1, the water leakage can be detected by using the electrostatic capacity value changed based on a dielectric constant of the water. In a case where the floor is formed of the carpet, when the water is oozed from the carpet below the outer bottom surface CB of the case 2, the water leakage can be similarly detected by using the electrostatic capacity value changed based on the dielectric constant of the water. Accordingly, it may be possible to detect the water leakage quickly on both of the flooring and the carpet.

Further, when the water is located at the side of the outer bottom surface CB of the housing separated from the mount surface by a length of the stud 3, the electrostatic capacity sensor 6 detects the change of the electrostatic capacity between the bottom portion of the case 2 and the mount surface, and thereby it may be possible to detect the water leakage in a case where the water is not directly contacted with the electrostatic capacity sensor 6. Accordingly, it may be possible to detect the water leakage quickly, and to restrict the spread of the damage at minimum. Further, since the electrostatic capacity sensor 6 and the electronic component are arranged in the case 2, those components can be completely separated from water. When the water leakage is detected, water dose not adhere to the electrostatic capacity sensor 6 and therefore the electrostatic capacity sensor 6 is not deteriorated due to a foreign object in the water. Since the water does not adhere to the electronic component, the circuit is not short-circuited. Accordingly, it may be possible to use the water leakage detector repeatedly for several times for a long period of time.

Since the height of the stud 3 is set in a range between 1 mm and 5.4 mm, specifically set to 2 mm, the water contacted with the side surface of the case 2 is apt to be introduced into a center side of the outer bottom surface CB, and thereby the detection sensitivity is improved. Further, since the multiple water introducing grooves 12 arranged at the outer bottom surface CB of the case 2 and arranged parallel with an interval is formed, the water apt to be spread on the mount surface is kept in a state of a water droplet, and the water can be sucked toward the outer bottom surface CB. With this, the water leakage can be detected quickly. Further, since the multiple water introducing grooves 12 are arranged at least in each of directions orthogonal to each other, even if the water approaches from various directions, it may be possible to quickly detect the water leakage.

Further, since the water introducing grooves 12 are formed between the detection electrode 7 and the ground electrode 8 of the electrostatic capacity sensor 6, the water introduced by the water introducing grooves 12 is moved as close as possible to a portion between the detection electrode 7 and the ground electrode 8, the portion having the highest detection sensitivity, and therefore the water leakage can be detected quickly. In addition, since the detection electrode 7 is divided into multiple parts, a change rate of the electrostatic capacity when the water approaches each of the detection electrodes 7a to 7d becomes large, and therefore the water leakage can be detected quickly.

Further, since the water preventing groove 13 is formed to connect end portions of the water introducing grooves 12 at a side of the center of the case 2, the water introduced by the water introducing groove 12 is prevented from moving to a center portion of the case 2, and therefore the water is apt to be retained between the detection electrode 7 and the ground electrode 8 located at the outer peripheral portion. Accordingly, it may be possible to firmly detect the water leakage.

Second to Fourth Embodiments

Figure 17:
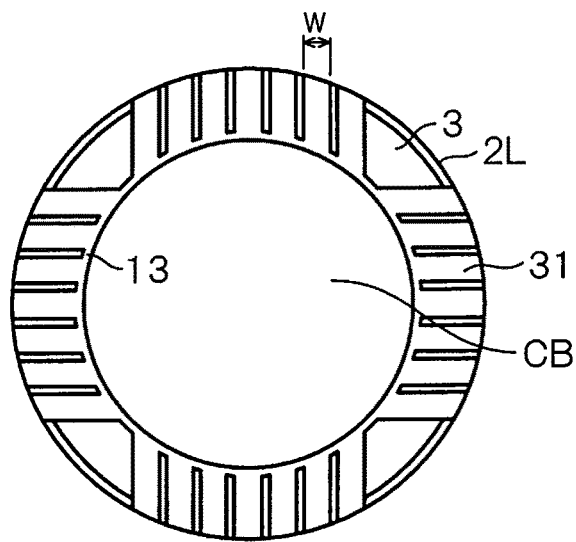
FIG. 17 is a bottom view of a lower case according to at least one of embodiments.

Second to fourth embodiments described below correspond to variations of a formation pattern of a groove. In the second embodiment shown in FIG. 17, a width W (=x) of a groove 31 is set to 4.0 mm. In this way, the water may be sucked into the groove 31 by expanding the width W.

Figure 18:
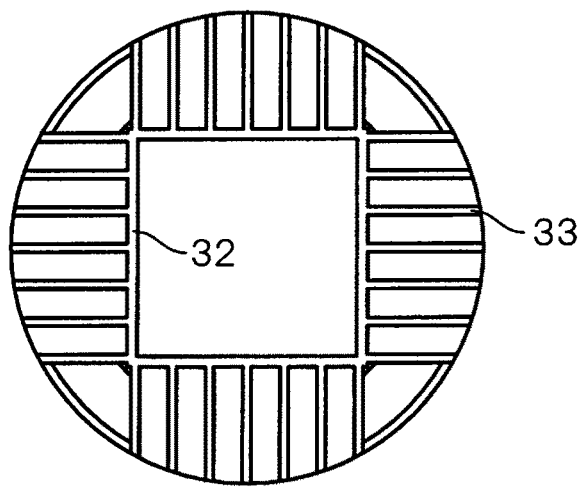
FIG. 18 is a bottom view of a lower case according to at least one of embodiments.

In the third embodiment shown in FIG. 18, a water preventing groove 32 is formed in a square frame shape and a length of the water preventing groove 32 is set to be longer than a length of a water introducing groove 33.

Figure 19:
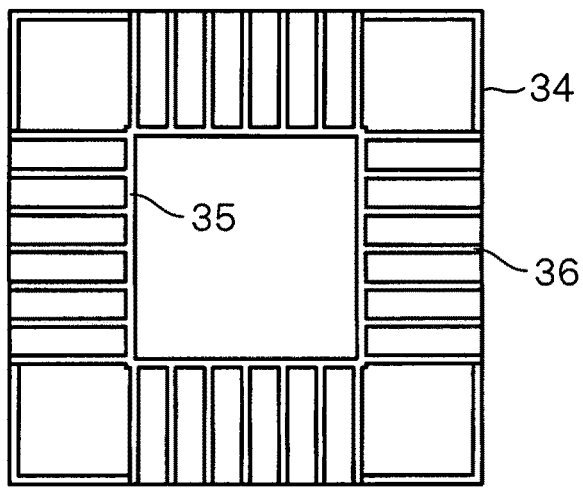
FIG. 19 is a bottom view of a lower case according to at least one of embodiments.

In the fourth embodiment shown in FIG. 19, an outer shape of the case 34 is formed in a square shape, and a water preventing groove 35 and a water introducing groove 36 are formed to correspond to the outer shape of the case 34 with the same pattern in the third embodiment.

The prevent disclosure is not limited to the embodiments described above or shown in the drawings, and therefore a modification and an expansion thereof as described below may be adopted.

The dividing number of the detection electrode 7 is not limited to four. Further, the detection electrode 7 is not necessarily divided, and therefore a doughnut shape shown in FIG. 7 may be adopted.

Each of the height h of the stud 3, the width W and the interval x of the water introducing groove 12 and the like may be modified in accordance with individual design as needed. Further, the pattern of the grooves 12, 13 formed at the outer bottom surface CB may be modified as needed. Further, the water preventing groove 13 is not necessarily formed, and both of the grooves 12 and 13 may not be formed.

The number of the studs 3 is not limited to four, and the number of the studs 3 may be set to three, or five or more.

According to one example of the present disclosure, a water leakage detector includes an electrostatic capacity sensor and a log portion. The electrostatic capacity sensor is arranged at a bottom portion of a housing. The leg portion provides a space between the bottom portion of the housing including the electrostatic capacity sensor and a floor.

With such a configuration, when the water leakage detector is arranged on the floor such as flooring and a carpet, an air layer is formed between the bottom portion of the housing and the floor. Thus, the electrostatic capacity sensor acquires an electrostatic capacity value based on a dielectric constant of air in a state where the water leakage does not occur. In a case where the floor is formed of the flooring, when water is entered into the space below the bottom portion of the housing of the water leakage detector, it may be possible to detect the water leakage by using the electrostatic capacity value changed based on a dielectric constant of the water. In a case where the floor is formed of the carpet, when the water is oozed from the carpet below the bottom portion of the housing, it may be possible to detect the water leakage similarly by using the electrostatic capacity value changed based on the dielectric constant of the water. It may be possible to detect the water leakage quickly on both of the flooring and the carpet.

According to another example of the present disclosure, a water leakage detector includes an electrostatic capacity sensor and an electronic component, and multiple leg portions. The an electrostatic capacity sensor is arranged at an inner bottom of a housing. The electronic component performs communication processing or input processing of the electrostatic capacity sensor, the electronic component being arranged in the housing. The multiple leg portions are arranged at outer bottom surface of the housing.

With such a configuration, when the water is located at the bottom portion of the housing separated from the mount surface of the water leakage detector by a length of the leg portion, the dielectric constant between the bottom portion of the housing and the mount surface is changed from the value of air to the value of water, and therefore the electrostatic capacity is changed. The electrostatic capacity sensor detects the change of the electrostatic capacity, and thereby it may be possible to detect the water leakage in a case where the water is not contacted with the sensor directly. Accordingly, it may be possible to detect the water leakage quickly, and to restrict the spread of the damage at minimum.

Assume that the sensor is arranged outside the housing, for example. In that case, the sensor may be deteriorated by contacting with water, and a circuit may be short-circuited when water enters the housing since a hole through connecting the sensor with an electronic device is necessary. It may be important to take measures against water in a case where the water leakage is detected by using the electronic device.

Furthermore, in the water leakage detector, since the electrostatic capacity sensor and the electronic component are arranged in the housing, it may be possible to completely separate those components from water. When the water leakage is detected, the water does not adhere to the sensor and therefore the sensor is not deteriorated due to a foreign object in the water. Since the water does not adhere to the electronic component, the circuit is not short-circuited. Accordingly, it may be possible to use the water leakage detector repeatedly for several times for a long period of time.

Furthermore, in the water leakage detector, a height of the leg portion may be set in a range between 1 mm and 5.4 mm. The inventor of the present disclosure studied a distance between the floor and the outer bottom surface of the housing, the distance allowing the leaked water contacted with the side surface of the housing to be introduced into a center side of the outer bottom surface of the housing by measuring a contact angle, a height of a water droplet, or the like in a state where a fine water droplet is contacted with a several kinds of floors. As a result, the inventor found that the leg portion has a height in the range between 1 mm and 5.4 mm. That is, by setting the height of the leg portion to be equal to or more than 1 mm, the water droplet can be firmly introduced into the center side of the outer bottom surface of the housing, and by setting the height of the leg portion to be equal to or less than 5.4 mm, a change degree of the dielectric constant of the introduced water becomes large, and therefore it may be possible to firmly detect the water leakage.

Furthermore, the water leakage detector may further include multiple water introducing grooves arranged at an outer bottom surface of the housing, the water introducing grooves being arranged parallel with each other at intervals. When water is changed into a water droplet, the water droplet has minimum surface area and becomes stable in energy. Thus, by arranging the multiple grooves in a parallel manner, the water apt to be spread on the mount surface is kept in a state of a water droplet, and the water can be sucked toward the side of the outer bottom surface of the housing. With this, it may be possible to detect the water leakage quickly.

Furthermore, in the water leakage, the water introducing grooves may be arranged between the detection electrode and the ground electrode of the electrostatic capacity sensor. With such a configuration, the water introduced by the water introducing grooves is moved as close as possible to a portion between the detection electrode and the ground electrode of the electrostatic capacity sensor, the portion having highest detection sensitivity, and therefore it may be possible to detect the water leakage quickly.

Furthermore, in the water leakage detector, the water introducing grooves may be arranged at least in each of directions orthogonal to each other. With such a configuration, even if the water approaches from various directions, it may be possible to detect the water leakage quickly. Further, since the leaked water is attracted also in a direction crossing a direction in which the water is entered due to a capillary phenomenon, the water is apt to be retained at an intersection point of both of the directions. Since the sensor is arranged above this point, it may be possible to detect the change of the electrostatic capacity due to the change of the dielectric constant easily.

Furthermore, in the water leakage detector, the detection electrode may be divided into multiple parts. With such a configuration, parasitic capacity in a state where the water does not approach the water leakage detector becomes small. The water leakage detection is performed based on the difference between the electrostatic capacity in a state where the water does not approach and the electrostatic capacity in a state where the water approaches. Accordingly, a change rate of the electrostatic capacity when the water approaches each of the detection electrodes becomes large, and therefore it may be possible to detect the water leakage quickly.

Furthermore, in the water leakage detector, a water preventing groove may be formed to connect end portions of the water introducing grooves at a side of the center of the housing. With such a configuration, the water introduced by the water introducing grooves is prevented from moving to a center portion of the housing, and therefore the water is easily retained between the detection electrode and the ground electrode located at the outer peripheral portion. Accordingly, it may be possible to detect the water leakage firmly.

It is noted that a flowchart or the process of the flowchart in the present application includes steps (also referred to as sections), each of which is represented, for instance, as S1. Further, each step can be divided into several sub-steps while several steps can be combined into a single step.

While the embodiments, the configurations, the aspects of an water leakage detector have been described by way of example, it should be appreciated that embodiments, configurations, aspects of the present disclosure are not limited to the respective embodiments, the respective configurations, and the respective aspects described above. For example, embodiments, configurations, aspects obtained by appropriately combining technical portions disclosed in different embodiments, configurations, and aspects are included within a range of embodiments, configurations, and aspects of the present disclosure.

What is claimed is:

1. A water leakage detector comprising:
an electrostatic capacity sensor that is arranged at a bottom portion of a housing, the electrostatic capacity sensor detecting a water leakage without electrodes of the electrostatic capacity sensor contacting the water; and
a leg portion that provides a space between a floor and the bottom portion of the housing including the electrostatic capacity sensor.

2. The water leakage detector according to claim 1, wherein:
a height of the leg portion is set in a range between 1 mm and 5.4 mm.

3. The water leakage detector according to claim 1, further comprising:
a plurality of water introducing grooves that are arranged at an outer bottom surface of the housing, the water introducing grooves being arranged parallel to each other at an interval.

4. The water leakage detector according to claim 3, wherein:
the electrodes of the electrostatic capacity sensor include a detection electrode and a ground electrode that are arranged at an outer peripheral portion of the housing; and
the water introducing grooves are provided between the detection electrode and the ground electrode.

5. The water leakage detector according to claim 3, wherein:
the plurality of water introducing grooves are arranged in groups, at least some of the groups extending in directions orthogonal to each other.

6. The water leakage detector according to claim 4, wherein:
the detection electrode is divided into a plurality of parts.

7. The water leakage detector according to claim 3, wherein:
the plurality of water introducing grooves include a water preventing groove that is configured to connect end portions of the water introducing grooves at a side of a center of the housing.

8. A water leakage detector comprising:
an electrostatic capacity sensor that is arranged at an inner bottom of a housing, the electrostatic capacity sensor detecting a water leakage without electrodes of the electrostatic capacity sensor contacting the water;
an electronic component that is arranged in the housing and performs communication or input processing of the electrostatic capacity sensor; and
a plurality of leg portions that are arranged at an outer bottom surface of the housing.

9. The water leakage detector according to claim 8, wherein:
a height of the leg portions is set in a range between 1 mm and 5.4 mm.

10. The water leakage detector according to claim 8, further comprising:
a plurality of water introducing grooves that are arranged at the outer bottom surface of the housing, the water introducing grooves being arranged parallel to each other at an interval.

11. The water leakage detector according to claim 10, wherein:
the electrodes of the electrostatic capacity sensor include a detection electrode and a ground electrode that are arranged at an outer peripheral portion of the housing; and
the water introducing grooves are provided between the detection electrode and the ground electrode.

12. The water leakage detector according to claim 10, wherein:
the plurality of water introducing grooves are arranged in groups, at least some of the groups extending in directions orthogonal to each other.

13. The water leakage detector according to claim 11, wherein:
the detection electrode is divided into a plurality of parts.

14. The water leakage detector according to claim 10, wherein:

the plurality of water introducing grooves include a water preventing groove that is configured to connect end portions of the water introducing grooves at a side of a center of the housing.

* * * * *